United States Patent [19]

Porro

[11] Patent Number: 5,358,933
[45] Date of Patent: Oct. 25, 1994

[54] SYNTHETIC PEPTIDES FOR DETOXIFICATION OF BACTERIAL ENDOTOXINS AND FOR THE PREVENTION AND TREATMENT OF SEPTIC SHOCK

[75] Inventor: Massimo Porro, Siena, Italy
[73] Assignee: BiosYnth S.r.l., Siena, Italy
[21] Appl. No.: 49,871
[22] Filed: Apr. 19, 1993

Related U.S. Application Data

[63] Continuation of Ser. No. 658,744, Feb. 11, 1991, abandoned.

[51] Int. Cl.$^5$ .................. A61K 37/02; C07K 7/06
[52] U.S. Cl. .................................. 514/15; 514/16; 514/17; 530/319; 530/327; 530/328; 530/329
[58] Field of Search ............. 530/329, 319, 328, 327; 514/15, 16, 17

[56] References Cited

U.S. PATENT DOCUMENTS 3,753,970  8/1973  Bouchaudon et al. .............. 530/319
3,817,973  7/1974  Bouchaudon et al. .............. 530/319

FOREIGN PATENT DOCUMENTS

WO117763  11/1991  PCT Int'l Appl.

OTHER PUBLICATIONS

Search Report, Sep. 9, 1992.
Antimicrobial Agents and Chemotherapy, vol. 30, No. 2, Aug. 1986, Duwe et al, "In vitro Cytotoxicity And Antibiotic Activity of Polymyxin B Nonapeptide", pp. 340–341.
Nature, vol. 303, Aug. 1983, Vaara et al, "Sensitization of Gram–negative Bacteria to Antibiotics and Complement by a Nontoxic Oligopeptide", pp. 526–528.
Antimicrobial Agents and Chemotherapy, vol. 33, No. 9, Sep. 1989, Danner et al, "Purification, Toxicity, and Antiendotoxin Activity of Polymyxin B Nonapeptide", pp. 1428–1434.
PCT Search Report, Jun. 18, 1992, Examiner Marshall.
J. Biol. Chem., vol. 263, No. 32, pp. 16709–16713 (1988).
J. Biol. Chem., vol. 265, No. 32, pp. 21350–21354 (1990).
J. Biol. Chem., vol. 252, No. 1,2, pp. 121–124 (1989).
Danner et al., Antimicrobial Agents and Chemotherapy, vol. 33, No. 9, pp. 1428–1434 (1989).
Viljanen et al., Infection and Immunity, vol. 56, No. 9, pp. 2324–2329 (1988).
Duwe et al., Antimicrobial Agents and Chemotherapy, vol. 30, No. 2, pp. 340–341 (1986).
Vaara et al., Nature, vol. 33, pp. 526–528 (1983).
Storm et al., Ann. Rev. Biochem., vol. 46, pp. 723–763 (1977).

*Primary Examiner*—Lester L. Lee
*Assistant Examiner*—S. G. Marshall
*Attorney, Agent, or Firm*—Hedman, Gibson & Costigan

[57] ABSTRACT

Novel peptides are disclosed which are based on the formula:

$$R_1(\text{Lys-Phe-Leu})_n\text{—R}$$

wherein n is an integer of from 1–10 and R and $R_1$ are H or an amino acid residue or a fatty acid residue which are useful in the treatment of septic shock.

16 Claims, No Drawings

SYNTHETIC PEPTIDES FOR DETOXIFICATION OF BACTERIAL ENDOTOXINS AND FOR THE PREVENTION AND TREATMENT OF SEPTIC SHOCK

This application is a continuation of application Ser. No. 07/658,744, filed Feb. 11, 1991, now abandoned.

BACKGROUND OF THE INVENTION

Shock, which is induced by endotoxin, is known as septic shock (SS). This condition is a life-threatening situation which occurs following infections by Gram-negative bacteria as complication of surgery, prolonged hospitalization, accidents and other traumatic events. It is today well recognized that the agent responsible for this disease is the bacterial endotoxin, a glycolipid antigen present only on the surface of Gram-negative bacteria. This glycolipid is also known as lipo-poly saccharide (LPS) or lipo-oligosaccharide (LOS) depending from the size of the carbohydrate chain which is covalently bound to the fatty-acid-rich moiety called Lipid A (LipA). Only Lipid A is responsible of the major toxic effects shown by endotoxin (LPS). Once endotoxin is released in the blood-stream by bacteria, specialized cells of the immune system like macrophages and monocytes are activated by the endotoxin and several immune mediators are released (Interleukine-1 and Interleukine-6;$\alpha$- Tumor necrosis factor;$\delta$- Interferon). Furthermore, endotoxin also activates the complement cascade which results in cell lysis with the consequent release of proteolytic enzymes promoting the release of vasoactive effectors from platelets (e.g.: bradykinine and histamine). The final result is death of the patient in 40–60% of the cases within 48–72 hours. So far, there has been no specific cure or therapy available although bolus injections of adrenal corticosteroids such as methylprednisolone are used.

Polymyxin "B" is known as a molecule that binds and detoxifies bacterial endotoxins and can prevent septic shock when given therapeutically in animal models. However, Polymyxin "B" is a toxic product in vitro and in vivo and this fact limits its potential as a therapeutic agent for the treatment of septic shock.

Septic shock can be caused by infection with any bacteria that cause the release of LPS. These bacteria include *Pseudomonas aeroginosa, Escherichia coli, Salmonella typhi, Neisseria meningitidis, Neisseria gonorrheae, Bordetella pertussis, Klebsiella pneumoniae* and the like.

The reasons leading to the reported toxicity are not completely understood but they are most likely related to the peculiarity of its amino acid composition, specifically for the content of L $\alpha$- $\delta$-, diamino butyric acid (DAB) (49.1% w/w of the structure) which is an analog of the aa Lysine (reported in literature as able to substitute Lysine in the protein synthesis) and for the presence of D-Phenylalanine an isomer of the naturally occurring L-Phenylalanine. Other possible reasons, still related to the aa composition, could be related to the high stability of Polymyxin "B" to proteolytic enzymes as well as to the possible binding to cell receptors structurally comparable to the Lipid A moiety of LPS (the gangliosides of the nervous tissues are glycolipids with N,O - acyl ($C_{14}$–$C_{18}$) chains closely related to the N,O - acyl chains present in the Lipid A structure). Condition other than septic shock where an endotoxin is produced may also be treated by the peptides of the invention. These conditions include pertussis bacterial meningitis and vital HIV-related infections.

The applicants have discovered new conformational peptides that are structurally different from Polymyxin (in virtue of their amino acid composition) but are capable of binding to the same binding site within Lipid A of endotoxins (LOS and LPS that Polymyxin "B" will also bind. The relative binding efficiency of the new peptides is comparable to the affinity constant value of Polymyxin "B".

As a consequence of this high-affinity binding to the Lipid A moiety of endotoxins, most of the synthetic peptides have shown the ability to detoxify endotoxins as evidenced by in vitro as well as in vivo analysis. The in vitro test used, as measure of detoxification, the inhibition of the enzymatic cascade leading to the coagulation of the Lymulus lysate (LAL test) by endotoxin. The LAL test is recognized as the most sensitive and predictive test for the toxic and pyrogenic activity of LPS, since pyrogenicity in vivo is related to the release of the endogenous immune modulators Interleukine-1 (IL-1) and alfa-Tumor necrosis factor ($\alpha$-TNF), the mediators responsible for the fatalities associated to septic shock. As an in vivo test confirming detoxification of LPS, was then used the Rabbit pyrogen test performed according to the United States Pharmacopeia XXI.

This discovery thus provides a new class of compounds that may be used in the treatment of septic shock. It is anticipated that the new peptides will not exhibit in humans the toxic effects of Polymyxin "B", in virtue of their completely natural amino acid composition as well as for their limited resistance to proteolytic degradation in human serum.

Accordingly, it is a primary object of the invention to provide novel therapeutic agents which may be used in the treatment of septic shock.

It is also an object of this invention to provide novel peptide compounds which may be used in the treatment of septic shock.

It is also an object of this invention to provide novel pharmaceutical compositions which may be used in the treatment of septic shock.

These and other objects of the invention will become apparent from a review of the present specification.

DETAILED DESCRIPTION OF THE INVENTION

The invention provides novel monomeric, linear polymeric, cyclic monomeric or cyclic polymeric peptides of the formula having amphipathic - polycationic characteristics:

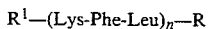

$R^1$—(Lys-Phe-Leu)$_n$—R wherein n is an integer of from 1–100 preferably 1–10 and R and $R^1$ are H or may be any of the naturally occurring amino acids or fatty acids with an alkyl chain length encompassing between 1 and 20 (or more) methylene groups; those peptides which have the retro-oriented aa sequences of the described peptides; those peptides which have the enantiomer aa sequences or diastereomer aa sequences of the described peptides; and those peptides which have the aa shifted in place with regard to their original positions which provide a peptide which is useful in the treatment of septic shock.

Specific examples of these peptides include:

```
Cys—Lys—Phe—Leu—Lys—Lys—Cys
 S  -  -  -  -  -  -  -  -  -  -  S    SEQ ID NO: 1

Lys—Thr—Lys—Cys—Lys—Phe—Leu—Lys—Lys—Cys
             S  -  -  -  -  -  -  -  -  -  -  S    SEQ ID NO: 2

Lys—Phe—Leu—Lys—Lys—Thr SEQ ID NO: 3

Ile—Lys—Thr—Lys—Lys—Phe—Leu—Lys—Lys—Thr SEQ ID NO: 4

Cys—Lys—Lys—Leu—Phe—Lys—Cys—Lys—Thr—Lys
 S  -  -  -  -  -  -  -  -  -  -  S

Cys—Lys—Lys—Leu—Phe—Lys—Cys—Lys—Thr
 S  -  -  -  -  -  -  -  -  -  -  S SEQ ID NO: 6

Ile—Lys—Thr—Lys—Cys—Lys—Phe—Leu—Lys—Lys—Cys
                 S  -  -  -  -  -  -  -  -  -  -  S    SEQ ID NO: 7

Ile—Lys—Phe—Leu—Lys—Phe—Leu—Lys—Phe—Leu—Lys SEQ ID NO: 8
```

R and $R^1$ may be any of the naturally occurring amino acids or fatty acids with an alkyl chain length encompassing between 1 and 20 (or more) methylene groups.

The novel peptides are useful for the prophylaxis or treatment of septic shock in mammals including humans at a dose of about 0.1 to about 15 μg/kg of body weight, preferably from about 1.0 to about 10 μg/kg body weight and most preferably about 15 μg/day/kg of body weight in divided doses. The peptides may be administered prophylactically to patients who may be exposed to or have been exposed to organisms which may cause septic shock. The particular dose of a particular peptide may be varied within or without the range that is specified herein depending on the severity of the disease and the condition of the host. Those who are skilled in the art may ascertain the proper dose using standard procedures.

The compounds may be administered intravenously and parenterally using well known pharmaceutical carriers or inert diluents. Oral administration is not preferred because the peptides will tend to be degraded by the enzymes of the alimentary tract. Water or isotonic saline are preferred diluents and a concentration of 0.1 mg per ml may be used. Preferably, the compounds SEQ. ID NO: 5 will be stored in a dry form and will be dissolved in the diluent immediately prior to administration.

The novel peptides may be synthesized by classical methods of peptide chemistry using manual or automated techniques as well as by DNA recombinant technology. The synthetic procedure comprises solid phase synthesis by Fmoc chemistry, cleavage (TFA 95%+Et-(SH)$_2$ 5%), followed by vacuum evaporation. Thereafter, the product is dissolved in 10% acetic acid, extracted with ether, concentrated at 0.1 mg/ml at pH of 6.0-7.5. Stirring followed for 1 to 6 hours and finally desalting by reverse phase chromatography occurred.

The activity of the peptides has been confirmed by the direct microprecipitin assay with *B. pertussis* Lipid A, and *B. pertussis* LPS. In addition, the binding activity for LPS as compared to Polymyxin "B" has been demonstrated on the basis of the ratio of peptide/LPS and peptide/Lipid A on a w/w basis. The data from the Limulus (LAL) test shows that the novel compounds, when tested at a proper concentration, have equivalent LAL inhibition to Polymyxin "B".

In addition, the novel compounds have been shown to be relatively unstable in the presence of proteolytic enzymes such as trypsin while it has been confirmed that Polymyxin "B" is stable in the presence of trypsin. These results show that the novel compounds are useful for the treatment of septic shock.

DESCRIPTION OF THE PREFERRED EMBODIMENTS

The following exemplifies the preferred procedure for the synthesis of the compounds of the invention.

Using the following procedure, peptides have been synthesized using the automatic synthesizer MILLIGEN Mod. 9050 (MILLIPORE, Burlington, Mass.) on a solid phase support of polyamide/Kieselguhr resin (2.0 g). The amino acids used in the synthesis of the peptide analogs were Fmoc-aa-Opfp derivatives (9-Fluorenylmethyloxycarbonyl-aa-O-pentafluorophenyl ester) of each amino acid (aa) involved in the considered sequences using 0.8 mmol of each amino acid to sequentially form the peptide.

Each cycle of synthesis was performed at r.t. (20° C.) and involved the following steps of reaction:

Step 1—Deprotection

The first aa Fmoc-protected at the amino group, was treated with a 20% solution of piperidine for 7 minutes in order to remove the Fmoc α-protecting group. Washing with dimethylformamide followed for 12 minutes to remove all traces of piperidine. Deprotection and washing were run continuously through the column containing the resin by mean of pump at a flow of 5 ml/min.

Step 2—Activation of the Fmoc-aa-Opfp derivative

The amino and carboxy-protected amino acid due, according to the desired sequence, was activated after its dissolution in 5 ml of dimethylformamide, by catalytic amount of hydroxybenzotriazol (0.5 ml of a 5% w/v solution in dimethylformamide).

Step 3—Acylation

The activated and protected Fmoc-aa-Opfp derivative was then recycled for 30 minutes through the column by the pump at 5 ml/min in order to obtain coupling of the introduced aa at the α-amino group (previously deprotected as reported in Step 1) of the amino acid preceding the new one in the desired sequence.

Step 4—Washing

Washing of the matrix in the column followed by dimethylformamide for 2 minutes at 5 ml/min before a new cycle began.

At the completion of the synthesis, the peptide on the resin support was cleaved by 95% Trifluoroacetic acid (TFA) with 5% Ethane dithiol as scavenger, if Cysteine residues were present in the aa sequence, at room temperature for 2 hours. After separation of the cleaved peptide from the resin by filtration, the solution was concentrated by vacuum evaporation to dryness. The collected solid residue was then solubilized in 10% acetic acid at a concentration of 10–20 mg/ml and several extractions by dimethyl ether followed (six to eight extractions with half of the volume of the peptide solution) in order to remove the scavenger Ethane dithiol. The peptide solution was then neutralized by 0.1N ammonium hydroxide and adjusted to the concentration of roughly 0.1 mg/ml. The solution was then stirred under air for 1 to 6 hours, in order to obtain the selective oxidation of the two sulphydryl groups belonging to the Cys residues of the sequence. In this way, only monomeric oxidized peptides were obtained with no traces of polymeric material. The solution of oxidized peptide was then desalted by reverse-phase chromatography on SEP-PAK C-18 cartridges (MILLIPORE) and finally freeze-dried. The products were analyzed by high-performance liquid chromatography (HPLC) analysis as well as by chemical analysis of the synthetic structures.

The following peptides were prepared using the procedure which has been set forth above:

Cys—Lys—Phe—Leu—Lys—Lys—Cys  I
S - - - - - - - - - - S   SEQ ID NO: 1

Lys—Thr—Lys—Cys—Lys—Phe—Leu—Lys—Lys—Cys  II
           S - - - - - - - - - - S   SEQ ID NO: 2

Lys—Phe—Leu—Lys—Lys—Thr SEQ ID NO: 3  III

Cys—Lys—Lys—Leu—Phe—Lys—Cys—Lys—Thr—Lys  IV
S - - - - - - - - - - S SEQ ID NO: 4

Cys—Lys—Lys—Leu—Phe—Lys—Cys—Lys—Thr  V
S - - - - - - - - - - S SEQ ID NO: 5

Ile—Lys—Thr—Lys—Cys—Lys—Phe—Leu—Lys—Lys—Cys  VI
         S - - - - - - - - - - S   SEQ ID NO: 6

Ile—Lys—Thr—Lys—Lys—Phe—Leu—Lys—Lys—Thr SEQ ID NO: 7  VII

Ile—Lys—Phe—Leu—Lys—Phe—Leu—Lys—Phe—Leu—Lys SEQ ID NO: 8  VIII

The amino acid composition of each peptide was determined by PICO-TAG and was found to be as follows:

TABLE I

| PEPTIDE | AMINO ACID | AMINO ACID COMPOSITION* (moles aa/mol peptide) | |
|---|---|---|---|
| | | EXPECTED | FOUND |
| I | Cys | 2.00 | 2.13 |
| | Leu | 1.00 | 1.06 |
| | Lys | 3.00 | 2.90 |
| | Phe | 1.00 | 1.01 |
| II | Cys | 2.00 | 2.16 |
| | Leu | 1.00 | 0.99 |
| | Lys | 5.00 | 4.95 |
| | Phe | 1.00 | 0.96 |
| | Thr | 1.00 | 1.03 |
| III | Leu | 1.00 | 0.98 |

TABLE I-continued

| PEPTIDE | AMINO ACID | AMINO ACID COMPOSITION* (moles aa/mol peptide) | |
|---|---|---|---|
| | | EXPECTED | FOUND |
| | Lys | 3.00 | 2.99 |
| | Phe | 1.00 | 1.01 |
| | Thr | 1.00 | 1.05 |
| IV | Cys | 2.00 | 2.15 |
| | Leu | 1.00 | 0.94 |
| | Lys | 5.00 | 4.97 |
| | Phe | 1.00 | 0.93 |
| | Thr | 1.00 | 1.10 |
| V** | Cys | — | 1.85 |
| | Leu | — | 0.94 |
| | Lys | — | 4.04 |
| | Phe | — | 0.98 |
| | Thr | — | 1.06 |
| VI | Cys | 2.00 | 2.14 |
| | Ile | 1.00 | 0.98 |
| | Leu | 1.00 | 0.99 |
| | Lys | 5.00 | 4.98 |
| | Phe | 1.00 | 0.94 |
| | Thr | 1.00 | 1.00 |
| VII | Ile | 1.00 | 0.98 |
| | Leu | 1.00 | 1.00 |
| | Lys | 5.00 | 4.99 |
| | Phe | 1.00 | 0.98 |
| | Thr | 2.00 | 2.00 |
| VIII | Ile | 1.00 | 0.98 |
| | Leu | 3.00 | 2.98 |
| | Lys | 4.00 | 3.92 |
| | Phe | 3.00 | 3.02 |

*Average of a minimum of three experiments.
**V is generated by tryptic hydrolysis in human serum from the synthetic analog IV.

All peptides of the above reported formulas were compared with Polymyxin "B" in a direct microprecipitin assay for Lipid A and LPS of *B. Pertussis* (5 μg each) in order to detect their precipitating (binding) activity:

TABLE II

| | μg | nmol | Complex ppt |
|---|---|---|---|
| Polymyxin "B" | 7.3 | 6.1 | + + + |
| Peptide I | 5.3 | 6.1 | + + − |
| Peptide II | 7.5 | 6.1 | + + + |
| Peptide III | 4.7 | 6.1 | + − − |
| Peptide IV | 7.5 | 6.1 | + + + |
| Peptide V | 7.5 | 6.1 | + + + |
| Peptide VI | 8.2 | 6.1 | + + + |
| Peptide VII | 7.5 | 6.1 | + + + |
| Peptide VIII | 8.7 | 6.1 | + + + |

Quantitation of the amount of precipitated peptides present in the complexes with LPS of B. pertussis has been done by amino acid analysis after acid hydrolysis (by 6M HCl) of the complexes recovered by centrifugation at 3,000 rpm ×15 minutes. In Table III, the stoichiometry of some complexes is reported as calculated by the ratio (on molar basis) between the amount of each peptide and the amount of Lipid A present in the structure of LPS used in the experiments:

TABLE III

STOICHIOMETRY OF THE COMPLEXES FORMED BETWEEN $LPS_{bp}$* AND SYNTHETIC PEPTIDE ANALOGS OF POLYMYXIN "B"

| | Amount of peptide** in the complex (nmoles) | Ratio peptide/LipA (mol/mol) |
|---|---|---|
| Polymyxin "B" | 2.69 | 1.02 |
| Peptide II | 3.39 | 1.28 |
| Peptide IV | 3.55 | 1.34 |
| Peptide VI | 3.12 | 1.18 |
| Peptide VII | 3.00 | 1.13 |
| Peptide VIII | 3.86 | 1.46 |

*Complexes formed between 10 ug of B. Pertussis LPS of B. Pertussis LPS (equivalent to 4.50 ug of Lipid A or 2.64 nmoles) and 10 ug of peptide (twice the amount corresponding to the saturation point found for Polymyxin "B" in the analysis of AFFINITY)
**Values represent the average of two separate experiments of amino acid analysis after acid hydrolysis of the recovered complexes.

To further characterize the binding activity of the synthetic peptides for Lipid A of endotoxin, experiments of direct competition with Polymyxin "B" have been set-up in order to evaluate the Affinity constant value of Polymyxin "B" for the toxic moiety of endotoxin and ultimately to calculate the Selectivity of the synthetic peptide analogs (ratio on molar basis, between the affinity constant value of a given peptide and that of Polymyxin "B" for Lipid A). Table IV shows the relative values of Affinity and those of Selectivity for the investigated peptides:

TABLE IV

CHARACTERISTICS OF THE COMPLEXES FORMED BETWEEN $LPS_{bp}$ AND SYNTHETIC PEPTIDE ANALOGS OF POLYMYXIN "B"

| Peptide | AFFINITY (Ka) (L/Moles) | SELECTIVITY ($Ka_{ANA}/Ka_{PCP}$) | AMOUNT OF ppt* |
|---|---|---|---|
| Polymyxin "B" | $1.15 \times 10^7$ | 1.0 | +++ |
| Peptide I | $<1.15 \times 10^5$ | <0.01 | ++− |
| Peptide II | $0.56 \times 10^7$ | 0.20 | +++ |
| Peptide VI | $0.29 \times 10^7$ | 0.33 | +++ |
| Peptide IV | $0.49 \times 10^7$ | 0.33 | +++ |
| Peptide VII | $0.19 \times 10^7$ | 0.17 | +++ |
| Peptide VIII | $1.29 \times 10^7$ | 1.13 | +++ |

*Detected as amount of precipitate obtained by microprecipitation in capillary tubes and by immunodiffusion in agarose.

The results obtained by the Limulus (LAL) test, shown in Table V, support the data obtained by measuring the Affinity of the peptides of the invention for the Lipid A moiety of LPS in that they were substantially equivalent to Polymyxin "B" in the inhibition of LPS activity on Limulus. The only peptide that showed a lower activity in the LAL inhibition was Peptide I which gave the lowest affinity constant value among the peptides reported in the present invention. Peptide I was, in fact, the one presenting the non complete structure needed for the mimick of Polymyxin "B" as the synthetic peptide analogs II, V, VI and VII have clearly shown in the previous Table IV. It is important to note that the LAL test is accepted by the most important institutions in the Public Health field (World Health Organization, United States Food and Drug Administration, etc.) as a predictive test for absence of pyrogenicity in injectable material and it can be used to replace the in vivo test of pyrogenicity in rabbits. As already mentioned in the background of the invention, the pyrogenic activity of LPS in vivo is due to the release from macrophages and monocytes of the immunomodulators Interleukine-1 and α- TNF, the leading molecules responsible for the fatal effects of septic shock.

TABLE V

INHIBITION OF LPS-INDUCED GELATION IN LAL TEST* BY SYNTHETIC PEPTIDES MIMICKING THE STRUCTURE OF POLYMYXIN "B"

| | LPS/Pept (w/w) | TEST** |
|---|---|---|
| LPS (0.1 μg LPS) | | POSITIVE |
| Polymyxin "B" (0.1 μg + LPS (0.1 μg) | 1 | NEGATIVE |
| Peptide I (0.1 μg) + LPS (0.1 μg) | 1 | POSITIVE |
| Peptide I (1.0 μg) + LPS (0.1 μg) | 10 | NEGATIVE |
| Peptide I (10.0 μg) + LPS (0.1 μg) | 100 | NEGATIVE |
| Peptide II (0.1 μg) + LPS (0.1 μg) | 1 | NEGATIVE |
| Peptide III (100 μg) + LPS (0.1 μg) | 1000 | POSITIVE |
| Peptide IV (0.1 μg) + LPS (0.1 μg) | 1 | NEGATIVE |
| Peptide VI (0.1 μg) + LPS (0.1 μg) | 2 | NEGATIVE |
| Peptide VII (0.1 μg) + LPS (0.1 μg) | 2 | NEGATIVE |

*The test had a sensitivity of 0.125 Endotoxin Units/ml equivalent in our case (LPS of B. Pertussis) to 0.4 ng/ml of LPS. The complexes were allowed to form at 37° C. for 30 minutes before to be processed for analysis after dilution 1/100 with saline.
**Values are representative of a minimum of three different analysis.

The results indicate that in order to mimick the structure of Polymyxin "B" for efficiently binding and detoxifying LPS, a synthetic peptide needs to have almost the complete aa sequence of Polymyxin "B" (Peptides II, IV, VI and VII contain ten and eleven aa residues versus ten aa residues of Polymyxin "B") with analogous (but not identical) chemical features. In contrast Peptide III, which contains only six aa residues (the linear sequence of the peptide-cycle in Polymyxin "B") is not able to efficiently bind and detoxify LPS. The minimal structure able to detoxify LPS appears to be Peptide I (corresponding to the peptide-cycle of Polymyxin "B") which, however, does not show an Affinity value comparable to the other peptide analogs showing a longer aa sequence.

The effects of trypsin present in human serum on Polymyxin "B" and the peptides of the invention was determined by combining 10 μl of human serum with 20 ug of the given peptide in 10 μl volume and holding the mixture at a temperature of 37° C. for different intervals of time. At various times, an aliquot of the mixture was processed by HPLC analysis in order to detect the residual amount of the investigated peptide. In Table VI the half-lives time of each peptide investigated are shown as compared to the half-life time of Polymyxin "B".

TABLE VI

STABILITY OF SYNTHETIC PEPTIDE ANALOGS OF POLYMYXIN "B" TOWARDS PROTEOLYSIS BY TRYPSIN IN HUMAN SERUM

| Peptide | Half-Life Time (t/2) (min) | AMOUNT RECOVERED after 180 mins (%) |
|---|---|---|
| Polymyxin "B" | >>180 | 100 |
| Peptide I | >180 | 70 |
| Peptide II | 50 | 10 |
| Peptide VI* | 1,080 (18 hours) | 76 |
| Peptide IV** | 18 | — |
| Peptide V | 240 | 55 |
| Peptide VII | 50 | 28 |

TABLE VI-continued

STABILITY OF SYNTHETIC PEPTIDE ANALOGS OF
POLYMYXIN "B" TOWARDS PROTEOLYSIS
BY TRYPSIN IN HUMAN SERUM

| Peptide | Half-Life Time (t/2) (min) | AMOUNT RECOVERED after 180 mins (%) |
|---|---|---|
| Peptide VIII | 7 | — |

*Tryptic hydrolysis of Peptide VI generates Peptide II
**Tryptic hydrolysis of Peptide IV generates Peptide V As already mentioned in the background of the invention, the pyrogenic activity of LPS in vivo is due to the release from macrophages and monocytes of the immune modulators Interleukine-1 (IL-1) and α-Tumor Necrosis Factor (α-TNF) the leading molecules responsible for the fatal effects of septic shock.

In order to experimentally verify this issue, we have injected four groups of three rabbits each, with the complexes formed by two representative synthetic peptides with LPS. The pyrogenicity test has been executed according to the United States Pharmacopeia (Vol. XXI)/The National formulary (Vol. XVI), Combined Edition, Jan. 1, 1985. As a negative control in the test, the complex formed by Polymyxin "B" and LPS was injected. As a positive control free LPS was injected. LPS has shown its peculiar pyrogenic activity starting the first hour from the injection and the temperature continued to increase until the third hour of observation as required by the test. The peculiar behavior of a febrile pattern induced by LPS, involves two waves of temperature increase (biphasic behavior): The first temperature increase (first wave) it is shown within two hours from the injection of LPS and it is due to the immediate impact of the antigen on the host's immune system. The second and more consistent temperature increase (second wave) appears in the third hour from the injection of LPS and it is mediated by the endogenous pyrogens IL-1 and α-TNF released from the immune competent cells stimulated by LPS. The two complexes formed with LPS by the Peptide I and Peptide II as well as by Polymyxin "B" did not show either of the two waves of temperature increase, demonstrating that the two immune mediators IL-1 and α-TNF were not released in vivo upon injection of (complexed) pyrogenic doses of LPS.

I claim:

1. A peptide of the formula:
Cys-Lys-Phe-Leu-Lys-Lys-Cys S----------S (SEQ ID NO:1)

2. A peptide according to which is of the formula:
Lys-Thr-Lys-Cys-Lys-Phe-Leu-Lys-Lys-Cys S----------S (SEQ ID NO:2)

3. A peptide which is of the formula:
Lys-Phe-Leu-Lys-Lys-Thr (SEQ ID NO:3)

4. A peptide which is of the formula:
Cys-Lys-Lys-Leu-Phe-Lys-Cys-Lys-Thr-Lys S---------S (SEQ ID NO:4)

5. A peptide which is of the formula:
Cys-Lys-Lys-Leu-Phe-Lys-Cys-Lys-Thr S----------S(SEQ ID NO:5)

6. A peptide which is of the formula:
Ile-Lys-Thr-Lys-Cys-Lys-Phe-Leu-Lys-Lys-Cys S---------S (SEQ ID NO:6)

7. A peptide which is of the formula:
Ile-Lys-Thr-Lys-Lys-Phe-Leu-Lys-Lys-Thr (SEQ ID NO:7)

8. A peptide which is of the formula:
Ile-Lys-Phe-Leu-Lys-Phe-Leu-Lys-Phe-Leu-Lys (SEQ ID NO:8)

9. A pharmaceutical composition which comprises a peptide of claim 1 and a pharmaceutical carrier.

10. A pharmaceutical composition which comprises a peptide of claim 2 and a pharmaceutical carrier.

11. A pharmaceutical composition which comprises a peptide of claim 3 and a pharmaceutical carrier.

12. A pharmaceutical composition which comprises a peptide of claim 4 and a pharmaceutical carrier.

13. A pharmaceutical composition which comprises a peptide of claim 5 and a pharmaceutical carrier.

14. A pharmaceutical composition which comprises a peptide of claim 6 and a pharmaceutical carrier.

15. A pharmaceutical composition which comprises a peptide of claim 7 and a pharmaceutical carrier.

16. A pharmaceutical composition which comprises a peptide of claim 8 and a pharmaceutical carrier.

* * * * *

UNITED STATES PATENT AND TRADEMARK OFFICE
CERTIFICATE OF CORRECTION

PATENT NO. : 5,358,933
DATED : October 25, 1994
INVENTOR(S) : Massimo PORRO

It is certified that error appears in the above-identified patent and that said Letters Patent is hereby corrected as shown below:

Column 1, line 30, "$\delta$" should be --$\gamma$--
Column 1, line 54, "$\delta$" should be --$\gamma$--
Column 2, line 2, "vital" should be --viral--
Column 3, line 6, "SEQ ID NO: 4" should be --SEQ ID NO: 7--
Column 3, line 8, insert (end of the line):--SEQ ID NO: 4--
Column 3, line 10, rewrite "6" as --5--
Column 3, line 12, rewrite "7" as --6--
Column 3, line 45, delete "SEQ. ID NO: 5"
Column 3, line 56, rewrite "followed" as --follows--
Column 3, line 57, rewrite "occurred" as --occurs--
Column 9, line 46, rewrite "TOPOOLOGY: circular" as --TOPOLOGY: linear--
Column 11, line 25, rewrite "TOPOLOGY: circular" as --TOPOLOGY: linear--
Column 11, line 33, rewrite "TOPOLOGY: circular" as --TOPOLOGY: linear--

UNITED STATES PATENT AND TRADEMARK OFFICE
CERTIFICATE OF CORRECTION

PATENT NO. : 5,358,933

DATED : October 25, 1994

INVENTOR(S) : Massimo PORRO

It is certified that error appears in the above-identified patent and that said Letters Patent is hereby corrected as shown below:

Rewrite Claims 1, 2, 4, 5 and 6 as follows:

Col. 11, lines 52 & 54

1. A peptide of the formula:

Cys-Lys-Phe-Leu-Lys-Lys-Cys

S-----------------------S   SEQ ID NO: 1

Col. 11, lines 56 & 58

2. A peptide of the formula:

Lys-Thr-Lys-Cys-Lys-Phe-Leu-Lys-Lys-Cys

S----------------------S   SEQ ID NO: 2

Col. 11 lines 61 & 63

4. A peptide which is of the formula:

Cys-Lys-Lys-Leu-Phe-Lys-Cys-Lys-Thr-Lys

S----------------------S   SEQ ID NO: 4

Col. 11 lines 64 & 66

5. A peptide which is of the formula:

Cys-Lys-Lys-Leu-Phe-Lys-Cys-Lys-Thr

S----------------------S   SEQ ID NO: 5

UNITED STATES PATENT AND TRADEMARK OFFICE
CERTIFICATE OF CORRECTION

PATENT NO.   : 5,358,933
DATED        : October 25, 1994
INVENTOR(S)  : Massimo PORRO It is certified that error appears in the above-identified patent and that said Letters Patent is hereby corrected as shown below:

Col. 11, lines 67 & 69
6. A peptide which is of the formula:
Ile-Lys-Thr-Lys-Cys-Lys-Phe-Leu-Lys-Lys-Cys
          S----------------------S   SEQ ID NO: 6

Signed and Sealed this

Third Day of October, 1995

Attest:

BRUCE LEHMAN

Attesting Officer            Commissioner of Patents and Trademarks

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 7 amino acids
( B ) TYPE: amino acid
( C ) TOPOLOGY: circular ( i i ) SEQUENCE DESCRIPTION: SEQ ID NO:1:

Cys  Lys  Phe  Leu  Lys  Lys  Cys
 1                 5

( 2 ) INFORMATION FOR SEQ ID NO:2:

( i ) SEQUENCE CHARACTERISTICS:
( A ) LENGTH: 10 amino acids
( B ) TYPE: amino acid
( C ) TOPOLOGY: circular ( i i ) SEQUENCE DESCRIPTION: SEQ ID NO:2:

Lys  Thr  Lys  Cys  Lys  Phe  Leu  Lys  Lys  Cys
 1                 5                           1 0

( 2 ) INFORMATION FOR SEQ ID NO:3:

( i ) SEQUENCE CHARACTERISTICS:
( A ) LENGTH: 6 amino acids
( B ) TYPE: amino acid
( C ) TOPOLOGY: circular ( i i ) SEQUENCE DESCRIPTION: SEQ ID NO:3:

Lys  Phe  Leu  Lys  Lys  Thr
 1                 5

( 2 ) INFORMATION FOR SEQ ID NO:4:

( i ) SEQUENCE CHARACTERISTICS:
( A ) LENGTH: 10 amino acids
( B ) TYPE: amino acid
( C ) TOPOLOGY: circular (i i) SEQUENCE DESCRIPTION: SEQ ID NO:4:

Cys Lys Lys Leu Phe Lys Cys Lys Thr Lys
 1           5                   10

(2) INFORMATION FOR SEQ ID NO:5:

(i) SEQUENCE CHARACTERISTICS:
 (A) LENGTH: 9 amino acids
 (B) TYPE: amino acid
 (C) TOPOLOGY: circular (i i) SEQUENCE DESCRIPTION: SEQ ID NO:5:

Cys Lys Lys Leu Phe Lys Cys Lys Thr
 1           5

(2) INFORMATION FOR SEQ ID NO:6:

(i) SEQUENCE CHARACTERISTICS:
 (A) LENGTH: 11 amino acids
 (B) TYPE: amino acid
 (C) TOPOLOGY: circular (i i) SEQUENCE DESCRIPTION: SEQ ID NO:6:

Ile Lys Thr Lys Cys Lys Phe Leu Lys Lys Cys
 1           5                   10

(2) INFORMATION FOR SEQ ID NO:7:

(i) SEQUENCE CHARACTERISTICS:
 (A) LENGTH: 10 amino acids
 (B) TYPE: amino acid
 (C) TOPOLOGY: circular (i i) SEQUENCE DESCRIPTION: SEQ ID NO:7:

Ile Lys Thr Lys Lys Phe Leu Lys Lys Thr
 1           5                   10

(2) INFORMATION FOR SEQ ID NO:8:

(i) SEQUENCE CHARACTERISTICS:
 (A) LENGTH: 11 amino acids
 (B) TYPE: amino acid
 (C) TOPOLOGY: circular (i i) SEQUENCE DESCRIPTION: SEQ ID NO:8:

Ile Lys Phe Leu Lys Phe Leu Lys Phe Leu Lys
 1           5                   10